(12) United States Patent
Millet et al.

(10) Patent No.: US 12,357,947 B2
(45) Date of Patent: Jul. 15, 2025

(54) SYSTEMS AND METHODS FOR TANGENTIAL FLOW FILTRATION OF VISCOUS COMPOSITIONS

(71) Applicant: ARC Medical Inc., Richmond (CA)

(72) Inventors: Ian Millet, Richmond (CA); Sailesh Haresh Daswani, Richmond (CA)

(73) Assignee: ARC Medical Inc., Richmond (CA)

( * ) Notice: Subject to any disclaimer, the term of this patent is extended or adjusted under 35 U.S.C. 154(b) by 312 days.

(21) Appl. No.: 17/260,285

(22) PCT Filed: Mar. 5, 2020

(86) PCT No.: PCT/CA2020/050295
§ 371 (c)(1),
(2) Date: Jan. 14, 2021

(87) PCT Pub. No.: WO2020/176990
PCT Pub. Date: Sep. 10, 2020

(65) Prior Publication Data
US 2022/0226779 A1    Jul. 21, 2022

Related U.S. Application Data

(60) Provisional application No. 62/814,212, filed on Mar. 5, 2019.

(51) Int. Cl.
*B01D 61/18* (2006.01)
*B01D 61/14* (2006.01)
*B01D 61/22* (2006.01)

(52) U.S. Cl.
CPC ........... *B01D 61/18* (2013.01); *B01D 61/145* (2013.01); *B01D 61/22* (2013.01);
(Continued)

(58) Field of Classification Search
None
See application file for complete search history.

(56) References Cited

U.S. PATENT DOCUMENTS 5,616,595 A    4/1997 Chu et al.
5,772,900 A    6/1998 Yorita et al.
(Continued)

FOREIGN PATENT DOCUMENTS

CA    2769147    2/2011
CN    1437650    8/2003
(Continued)

OTHER PUBLICATIONS

Abstracts of the 25th Annual Meeting of ESHRE, Amsterdam, The Netherlands, Jun. 28, 2009-Jul. 1, 2009.
(Continued)

*Primary Examiner* — Krishnan S Menon
(74) *Attorney, Agent, or Firm* — King IP Law; Joshua King

(57) ABSTRACT

Apparatus, methods, systems, etc., for the tangential flow filtration (TFF) of viscous compositions including viscous fluids, solutions, gels, pastes, creams and suspensions with viscosities greater than 10 cP, 20 cP, 50 cP or 100 cP. The methods, etc., provide enhanced mixing of the viscous compositions in their storage vessels by extracting the input composition from different depths in the storage vessels to reduce or eliminate vertical concentration gradients.

18 Claims, 6 Drawing Sheets

(52) U.S. Cl.
CPC ...... *B01D 2311/25* (2013.01); *B01D 2313/04* (2013.01); *B01D 2313/50* (2013.01); *B01D 2315/10* (2013.01); *B01D 2315/16* (2013.01); *B01D 2317/04* (2013.01)

(56) References Cited

U.S. PATENT DOCUMENTS

| | | | |
|---|---|---|---|
| 5,958,244 | A * | 9/1999 | Hartmann ............ B01D 61/025 |
| | | | 210/636 |
| 6,868,715 | B1 | 3/2005 | Carnahan et al. |
| 8,426,381 | B2 | 4/2013 | Thibodeau et al. |
| 8,466,125 | B2 | 6/2013 | Springate |
| 9,833,741 | B2 * | 12/2017 | Roh ...................... B01D 61/147 |
| 10,139,378 | B2 | 11/2018 | Kang |
| 2003/0085166 | A1 * | 5/2003 | Dreyer ...................... E03B 3/04 |
| | | | 210/220 |
| 2003/0224346 | A1 | 12/2003 | Karlsson |
| 2004/0014179 | A1 | 1/2004 | Thwaites |
| 2007/0122875 | A1 | 5/2007 | Sakai |
| 2007/0298508 | A1 | 12/2007 | Deslauriers et al. |
| 2008/0063682 | A1 | 3/2008 | Cashman et al. |
| 2009/0105910 | A1 | 4/2009 | Hatano et al. |
| 2009/0170801 | A1 | 7/2009 | Hao |
| 2009/0170810 | A1 | 7/2009 | Hao |
| 2011/0021457 | A1 | 1/2011 | Springate |
| 2011/0172156 | A1 | 7/2011 | Dockal et al. |
| 2015/0041395 | A1 * | 2/2015 | Oranth ................... B01D 61/20 |
| | | | 210/257.2 |
| 2017/0328873 | A1 | 11/2017 | Kang |
| 2018/0051097 | A1 | 2/2018 | Springate et al. |

FOREIGN PATENT DOCUMENTS

| | | | |
|---|---|---|---|
| CN | 1985846 | | 6/2007 |
| CN | 101011411 | | 8/2007 |
| CN | 101037483 | | 9/2007 |
| CN | 101156664 | | 4/2008 |
| CN | 101659709 | | 3/2010 |
| CN | 102665733 | | 9/2012 |
| CN | 102911281 | | 2/2013 |
| CN | 202778304 | | 3/2013 |
| CN | 104586878 | | 5/2015 |
| CN | 105399848 | | 3/2016 |
| CN | 106176798 | | 12/2016 |
| CN | 106832022 | | 6/2017 |
| CN | 107155305 | | 9/2017 |
| CN | 10738266 | | 11/2017 |
| CN | 207333195 | U * | 5/2018 |
| CN | 112513165 | | 7/2019 |
| EA | 201270186 | | 9/2012 |
| EA | 25808 | | 1/2017 |
| EP | 100843 | | 2/1984 |
| EP | 0567914 | | 11/1993 |
| EP | 1277834 | | 1/2003 |
| JP | 10182703 | | 7/1998 |
| JP | 2005507077 | | 3/2005 |
| JP | 2005508893 | | 4/2005 |
| JP | 2005517955 | | 6/2005 |
| JP | 2007504273 | | 1/2007 |
| JP | 2010519383 | | 6/2010 |
| JP | 2013500274 | | 1/2013 |
| JP | 2013517285 | | 5/2013 |
| JP | 2013180994 | | 9/2013 |
| JP | 2014124579 | | 7/2014 |
| JP | 2016505083 | | 2/2016 |
| JP | 2016128491 | | 7/2016 |
| JP | 2017206542 | | 11/2017 |
| JP | 2018513383 | | 5/2018 |
| KR | 20060031936 | | 4/2006 |
| KR | 20060051439 | | 5/2006 |
| KR | 20100138440 | | 12/2010 |
| KR | 20160011952 | | 2/2016 |
| KR | 101950246 | | 2/2019 |
| PH | 12012500177 | | 10/2012 |
| RU | 2247574 | | 3/2005 |
| RU | 2497525 | | 11/2013 |
| RU | 2591161 | | 7/2016 |
| RU | 2015135635 | | 3/2017 |
| RU | 2638859 | | 1/2018 |
| WO | WO2008031332 | | 3/2008 |
| WO | WO2008041799 | | 4/2008 |
| WO | WO2008103234 | | 8/2008 |
| WO | WO2010/110223 | | 9/2010 |
| WO | WO2011/011881 | | 2/2011 |
| WO | WO2014113836 | | 7/2014 |
| WO | WO2016/117599 | | 7/2016 |
| WO | WO2017/042603 | | 3/2017 |
| WO | WO2017/160739 | | 9/2017 |
| WO | WO2020/176989 | | 9/2020 |
| WO | WO2020176990 | | 9/2020 |

OTHER PUBLICATIONS

Ale et al., "Important Determinants for Fucoidan Bioactivity: A Critical Review of Structure-Function Relations and Extraction Methods for Fucose-Containing Sulfated Polysaccharides from Brown Seaweeds," Mar. Drugs, Oct. 24, 2011, vol. 9, pp. 2106-2130.

Baba et al., "Effects of extraction solvent on fucose content in fucoidan extracted from brown seaweed (*Sargassum* sp.) from Pulau Lankawi, Kedah, Malaysia," AIP Conference Proceedings, Nov. 17, 2016, vol. 1784, 030045, pp. 1-5.

Balboa et al., "Valorization of Sargassum muticum Biomass According to the Biorefinery Concept," Marine Drugs, Jun. 11, 2015, vol. 13, pp. 3745-3760.

Cashman, Johanne et al., "Fucoidan Film Safely Inhibit Surgical Adhesions in a Rat Model," Journal of Surgical Research, vol. 171, pp. 495-603, 2011.

Chen et al., "A new extraction method for fucoidan from the soaked water of brown seaweed (*Laminaria japonica*)," Desalination and Water Treatment, Feb. 2012, vol. 40:1-3, pp. 204-208.

Chizhov et al., "A study of fucoidan from the brown seaweed Chorda filum," Carbohydrate Research, Jul. 20, 1999, vol. 320, pp. 108-119.

Corrigan, N. et al., "Copolymers with Controlled Molecular Weight Distributions and Compositional Gradients through Flow Polymerization," Macromolecules, 2018, vol. 51(12), pp. 4553-4563.

Croci, D.O. et al., "Fucans, but not Fucomannoglucornonas, Determine the Biological Activities of Sulfated Polysaccharides from *Liminaria saccharina* Brown Seaweed," PLOS ONE, V. 6, I 2, e17283, pp. 1-10, downloaded Sep. 24, 2021, doi.org/10.1371/journal.pone.0017283.

Cumashi, Albana et al., "A comparative study of the anti-inflammatory, anticoagulant, antiangiogenic, and antiadhesive activities of nine different fucoidans from brown seaweeds," Glycobiology, vol. 17, No. 5, pp. 541-552.

Deniaud-Bouet, E. et al., "Chemical and enzymatic fractionation of cell walls from Fucals: insights into the structure of the extracellular matrix of brown algae," Annals of Botany, May 29, 2014, vol. 114, pp. 1203-1216.

Fernando et al., "A fucoidan fraction purified from Chnoospoora minima: a potential inhibitor of LPS-induced inflammatory responses," International Journal of Biological Marcromolecules, 2017, vol. 104, pp. 1185-1193.

Dorschmann, Phillip et al., "Effects of Sulfated Fucans from Laminaria hyperborean Regarding VEGF Secretion, Cell Viability, and Oxidative Stress and Correlation with Molecular Weight," Marine Drugs, 2019, vol. 17, No. 548, 14 pages.

Fitton, Janet et al., "Therapies from Fucoidan: An Update" Marine Drugs, vol. 13, No. 9, Sep. 6, 2016, pp. 5920-5946.

Fujikawa, Tatsuo et al., "Occurrence of Fucoidan and Fucoidan Analogues in Brown Seaweed," Agricultural Chemistry, vol. 49, No. 9, 1975, pp. 455-461.

Greco et al., "A Simple and Effective Method for High Quality Co-Extraction of Geonomic DNA and Total RNA from Low Biomass *Ectocarpus siliculosus*, the Model Brown Alga," PLOS One, May 27, 2014, vol. 9(5), pp. 1-13.

(56) References Cited

OTHER PUBLICATIONS

"Guidance for Industry, Estimating the Maximum Safe Starting Dose in Initial Clinical Trials for Therapeutics in Adult Healthy Volunteers," U.S. Department of Health and Human Services Food and Drug Administration Center for Drug Evaluation and Research (CDER), 2005, pp. 1-27.

Hahn et al., "Novel Procedures for the extraction of fucoidan from brown algae," Process Biochemistry, Jun. 23, 2012, vol. 47, pp. 1691-1698.

Haroun-Bouhedja et al., "Relationship between Sulfate Groups and Biological," Thrombosis Research, Dec. 1, 2000, vol. 100(5), pp. 453-459.

Hoagland, "The Complex Carbohydrates and Forms of Sulphur in Marine Algae of the Pacific Coast," The Journal of Biological Chemistry, 1915, vol. 23(1), pp. 287-297.

International Search Report and Written Opinion relating to International Patent Application No. PCT/CA2019/051026, mailed Oct. 16, 2019, 17 pages.

International Search Report and Written Opinion relating to International Patent Application No. PCT/CA2019/051027, mailed Nov. 20, 2019, 15 pages.

International Search Report and Written Opinion relating to International Patent Application No. PCT/CA2019/051030, mailed Nov. 27, 2019, 24 pages.

International Search Report and Written Opinion relating to International Patent Application No. PCT/CA2019/051028, mailed Nov. 15, 2019, 27 pages.

International Search Report and Written Opinion relating to International Patent Application No. PCT/CA2019/051029, mailed Dec. 12, 2019, 15 pages.

International Search Report and Written Opinion relating to International Patent Application No. PCT/CA2020/050294, mailed May 29, 2020, 8 pages.

International Search Report and Written Opinion relating to International Patent Application No. PCT/CA2020/050295, mailed Jun. 5, 2020, 12 pages.

Kim, et al., "Molecular weight and sulfate content modulate the inhibition of a-amylase by fucoidan relevant for type 2 diabetes management," PharmaNutrition, Jul. 2015, vol. 3(3), pp. 108-114.

Kopplin, Georg et al., "Structural Characterization of Fucoidan from Laminaria hyperborean: Assessment of Coagulation and Inflammatory Properties and Their Structure-Fucan Relationship," Applied Bio Materials, 2018, vol. 1. pp. 1880-1892.

Koyanagi et al., "Oversulfation of Fucoidan Enhances its Anti-Angiogenic and Anti-Tumor Activities," Biochemical Pharmacology, Jan. 15, 2003, vol. 65(2), pp. 173-179.

Lee et al., "Variation in Fucoidan Contents and Monosaccharide Compositions of Korean Undaria pinnatifida (Harvey) Surigar (Phaephyta)," Algae, vol. 21:1, 2006, 157-160.

Li et al., "Fucoidan: Structure and Bioactivity," Molecules, Aug. 12, 2008, vol. 13, pp. 1671-1695.

Ly et al., "Studies on Fucoidan and its Production from Vietnamese Brown Seaweeds," ASEAN Journal on Science and Technology for Development, 2005, vol. 22(4), pp. 371-380.

Mabeau, Serge et al., "Fractionation and Analysis of Fucans from Brown Algae", Phytochemistry, vol. 29, No. 8, pp. 2441-2445, 1990.

Makarenkova, I D et al., "Sulfated polysaccharides of brown seaweeds are ligands of toll-like receptors," Biochemistry (Moscow) Supplement Series B: Biomedical Chemistry, SP Maik Nauka, Interperiodica, Dordrecht, vol. 6, No. 1, Mar. 2012, pp. 75-80.

Men'Shova, R.V. et al., "Effect of pretreatment conditions of brown algae by supercritical fluids on yield and structural characteristics of fucoidans," Chemistry of Natural Compounds, Jan. 2013, vol. 48, No. 6, pp. 923-926.

Mulloy, Barbara et al., "Sulfated fucans from Echinoderms have a regular tetrasaccharide repeating unit defined by specific patterns of sulfation at the 0-2 and 0-4 positions Analysis View project," Oct. 1, 1994, DOI: 10.1016/S0021-9258 (17) 31763-5.

Nishino, Takashi et al., "Anticoagulant and antithrombin activities of oversulfated fucans," Carbohydrate Research, 229 (1992) 355-362.

Pereira, M.S. et al., "Is there a correlation between structure and anticoagulant action of sulfated galactans and sulfated fucans," Glycobiology, Oct. 1, 2002, vol. 12(10), pp. 573-580, downloaded from the internet https://doi.org/10.1093/glycob/cwf077.

Qiu et al., "Effect of oversulfation on the chemical and biological properties of fucoidan," Carbohydrate Polymers, Nov. 21, 2005, vol. 63, pp. 224-228.

Regis et al., "Regioselective desulfation of sulfated L-fucopyranoside by a new sulfoesterase from the marine mollusk Pecten maximus Application to the structural stud of agal fucoidan (Ascophyllum nodousm)," European Journal of Biochemistry, Aug. 19, 2003, vol. 268, pp. 5617-5626.

Saboural, P. et al. "Purification of a Low Molecular Weight Fucan for SPECT Molecular Imaging of Myocardial Infarction,", Marine Drugs 2014, vol. 12, pp. 4851-4867.

Sakai, Takeshi et al., Polymers, Jul. 2006, vol. 55, pp. 488-489.

Seimon, T.A. et al., "Combinational pattern recognition receptor signaling alters the balance of life and death in macrophages," PNAS Cell Biology (2006), vol. 103, No. 52, pp. 19794-19799.

Sezer, A.D. et al., "Preparation of fucoidan-chitosan hydrogel and its application as burn healing accelerator on rabbits," Biol Pharm Bull. 2008, vol. 31(12), pp. 2326-2333.

Simurant et al., "Purification and Characterization of Fucoidan From the Brown Seaweed *Sargassurn binderi sonder*," Squalen Bulletin of Marine & Fisheries Postharvest & Biotechnology, Aug. 2015, vol. 10(2), pp. 79-87.

Soeda et al., "Preparation of oversulfated fucoidan fragments and evaluations of their antithrombotic activities," Thrombosis Research, Nov. 1, 1993, vol. 72(3), pp. 247-256.

Soeda et al., "Oversulfated fucoidan and heparin suppress endotoxin induction of plasminogen activator inhibitor-1 in cultured human endothelial cells: their possible mechanism of action," Biochimica et Biophysica Acta (BBA)—Molecular Cell Research, Oct. 19, 1995, vol. 1269(1), pp. 89-90.

Usui et al., "Isolation of Highly Purified Fucoidan from Eisenia bicyclis and Its Anticoagulant and Antitumor Activities," Agric. Biol. Chem, Mar. 12, 1980, vol. 44(8), pp. 1965-1966.

Wang, "Impacts of Processing and Storage Methods on the Yield and Composition of Fucoidan from Undaria pinnatifida," Auckland University of Technology, Nov. 2014, pp. 1-71.

Wijesinghe et al., "Biological activities and potential industrial applications of fucose rich sulfated polysaccharides and fucoidans isolated from brown seaweeds: A review," Carbohydrate Polymers, Dec. 24, 2011, vol. 88. pp. 13-20.

Wu et al., "Liquid-Liquid Extraction of Fucoidan Leached from Brown Seaweeds," The Chinese Journal of Process Engineering, Feb. 2002, ISSN http://en.cnki.com.cn/Article_en/CJFDTotal-HGYJ200202006.htm.

Wu, "Solvent Extraction of Fucoidan in Aqueous Solution with Quaternary Ammonium Salt as Extractant," Chinese High Technology Letters, Aug. 2001, ISSN http://en.cnki.com.cn/Article_en/CJFDTotal-GJSX200108009.htm.

Wu et al., "Structural Analysis and Anticoagulant Activities of the Novel Sulfated Fucan Possessing a Regular Well-Defined Repeating Unit from Sea Cucumber," Marine Drugs, Apr. 13, 2015, vol. 13, p. 2063-2084.

Xing et al., "Extraction and Separation of Fucoidan from Laminaria japonica with Chitosan as Extractant," Hindawi Publishing Corporation, 2013, pp. 1-4.

Zayed et al., "Physiochemical and Biological Characterization of Fucoidan from Fucus vesiculosus Purified by Dye Affinity Chromatography," Marine Drugs, Apr. 15, 2016, vol. 14(4), pp. 1-15.

Zhang, H. et al., "Control of molecular weight distribution for polypropylene obtained by commercial Ziegler-Natta catalyst: effect of temperature," Polym. Bull. 2011, vol. 67, pp. 1519-1527.

Zhao, Yu et al., "Fucoidan Extracted from Undaria pinnatifida: Source for Nutraceuticals/Functional Foods," Marine Drugs, 2018, vol. 16: 321, 17 pages.

(56) References Cited

OTHER PUBLICATIONS

Zhao et al., "The Removal of Lead from Purified Fucoidan Extracted from Kelp Laminari japonica," Fisheries Science, Feb. 2012, ISSN http://en.cnki.com.cn/Article_en/CJFDTOTAL-CHAN201202011.htm.

* cited by examiner

SYSTEMS AND METHODS FOR TANGENTIAL FLOW FILTRATION OF VISCOUS COMPOSITIONS

CLAIM FOR PRIORITY

The present application claims the benefit of U.S. provisional patent application No. 62/814,212 filed Mar. 5, 2019, the content of which is incorporated herein by reference in their entirety.

BACKGROUND

Tangential flow filtration (TFF) is filtration where an input composition being filtered flows continuously along-side the filter (known as a "filter membrane"). In contrast, in "direct flow filtration" (also known as "dead end" filtration) the input composition flows directly into a filter held at the end of a tube or container, like a coffee filter held at the end/bottom of the brewing container. In TFF, anything that crosses (permeates) the filter membrane is known as the "permeate" and anything that stays on (is retained on) the initial side of the membrane is known as the "retentate". Typically, the filter membrane filters out smaller molecules that flow through the filter as a part of the permeate. Larger molecules are retained in the retentate. TFF is a good way to separate and/or purify "biomolecules", which are molecules such as proteins, polysaccharides and DNA that are obtained from biological sources.

One problem for both TFF and dead-end filters is that the filter tends to get clogged over time, which slows down the filtering across the filter membrane (also known as low permeate flow rates). One advantage of TFF is that, if done correctly, it can continuously wash away the clog: the constant flow of the input composition parallel to the filter membrane prevents the retained larger molecules from building up on the membrane surface. To avoid clogging, the flow rate of the input composition along the filter must be fast enough to keep the larger molecules from sticking to and building up on the filter membrane: the high flow rate sweeps them away. High flow rates, however, cause pressure to build-up at the input composition inlet. If the pressure builds up too much, it can cause the tubing bringing in the input composition and/or the input pump to fail.

It's difficult to accomplish large scale TFF of large biomolecules because they form highly viscous input compositions, which in turn causes high pressure build-up during the TFF process. Another problem with large biomolecules is that they settle to the bottom of storage tanks over time. This causes a "concentration gradient", which means that there are more biomolecules at the bottom of the container than the top, and which in turn means that the input composition at the bottom is more viscous than the input composition at the top. This causes inconsistent and even unexpected high-pressure problems, in addition to clogging the filter and long processing times.

Thus, there has gone unmet a need for improved systems, methods, etc., that improve the TFF of large biomolecules and/or protect TFF systems from pressure build up. The present systems and methods, etc., provide these and/or other advantages.

SUMMARY

Apparatus, methods, etc., are provided for improved, and aseptic if desired, TFF of viscous compositions including those comprising large biomolecules. Such viscous compositions include viscous fluids, solutions, gels, pastes, creams and suspensions, with viscosities greater than 10 cP, 20 cP, 50 cP or 100 cP, to be processed by the systems herein. High molecular weight fucan compositions are examples of biomolecules of considerable industrial interest. Viscous compositions can comprise high molecular weight fucan compositions, for example, solutions, gels, pastes, creams or suspensions comprising a quantity of high molecular weight fucan compositions that results in a composition-viscosity of greater than 10 cP, 20 cP, 50 cP or 100 cP. Fucans, such as fucoidan, are sulfated polysaccharides that are typically derived from seaweeds and that have been shown to be effective in treating fibrous adhesions and other medical conditions and/or disorders. Viscous compositions comprising fucans are exemplary input compositions to be processed by the systems discussed herein.

In some respects, the methods, systems, etc., may comprise a tangential flow filtration (TFF) system comprising:
  a tangential flow filtration (TFF) module;
  a storage vessel comprising an input composition;
  a tangential flow filtration input supply tube operably connected to deliver input composition from the storage vessel to the tangential flow filtration module; and
  a retentate return tube operably connected to return TFF retentate from the tangential flow filtration module to the storage vessel; wherein
  the tangential flow filtration (TFF) system further can comprise at least one aseptic seal such that that TFF system can be configured to aseptically deliver input composition from the storage vessel to the tangential flow filtration module and aseptically deliver TFF retentate back to the storage vessel.

In other aspects, the methods, systems, etc., may comprise a tangential flow filtration system comprising:
  a tangential flow filtration module;
  a storage vessel comprising an input composition;
  a tangential flow filtration input supply tube configured to deliver input composition from multiple depths within the storage vessel to the tangential flow filtration module, wherein the tangential flow filtration input supply tube can comprise a plurality of inlet ports disposed at different heights within the storage vessel; and
  a retentate return tube configured to return TFF retentate from the tangential flow filtration module to the storage vessel.

In further aspects, the methods, systems, etc., may comprise a tangential flow filtration system comprising:
  a tangential flow filtration module;
  a storage vessel comprising an input composition;
  a diafiltration vessel comprising a diafiltration solution;
  a tangential flow filtration input supply tube operably connected to deliver input composition from within the storage vessel to the tangential flow filtration module;
  a retentate return tube configured to return TFF retentate from the tangential flow filtration module to the storage vessel; and
  a diafiltration solution supply tube configured to deliver diafiltration solution from the diafiltration vessel to the retentate return tube upstream from the storage vessel.

In certain embodiments, the diafiltration solution supply tube can be configured to deliver diafiltration solution from the interior of the diafiltration vessel to the retentate return tube proximate the tangential flow filtration module. The diafiltration solution supply tube can be configured to deliver diafiltration solution from the interior of the diafiltration vessel to the retentate return tube via a Y-connector. The tangential flow filtration supply tube and the retentate return tube terminate at different depths in the interior of the storage vessel. The tangential flow filtration (TFF) system and tangential flow filtration (TFF) module can be configured to retain and filter a viscous composition without a substantial concentration gradient in the viscous composition.

In certain embodiments, the viscous composition can be a viscous solution. The viscous solution can have a viscosity of between about 10 centipoise and 5000 centipoise, 20 centipoise and 2000 centipoise, 40 centipoise and 1000 centipoise, 50 centipoise and 500 centipoise, or 10 centipoise and 200 centipoise.

In still further aspects, the methods, systems, etc., may comprise a tangential flow filtration system comprising a) a storage vessel fluidly connected to a tangential flow filtration module, and b) a recirculation system separate from the tangential flow filtration module and comprising a recirculation tube having a recirculation tube inlet disposed within the storage vessel at a depth selected to extract contents of the storage vessel and having a recirculation tube outlet disposed inside the storage vessel, wherein the recirculation system can be configured such that anything in the recirculation system does not pass through the tangential flow filtration module and wherein the recirculation tube inlet and the recirculation tube outlet can be located within in the storage vessel such that passage of the contents of the storage vessel through the recirculation system inhibits concentration gradients within the storage vessel.

The recirculation tube inlet and the recirculation tube outlet can be not connected to any tangential flow filtration module inlet or tangential flow filtration module outlet. The recirculation system further can comprise a recirculation system pump disposed to pump the contents of the storage vessel through the recirculation system, the recirculation system pump not connected to the tangential flow filtration module. The tangential flow filtration module inlet can comprise a plurality of inlet ports disposed at different locations along the tangential flow filtration module inlet, the different locations corresponding to substantially different depths within the storage vessel.

In certain embodiments, the systems can further comprise a recirculation system configured to extract and return the contents of the storage vessel to and from the storage vessel. A single supply tube can be configured to extract the contents of the storage vessel from the storage vessel and deliver the contents of the storage vessel to both the tangential flow filtration module and the recirculation system The recirculation system further can comprise a recirculation return tube. The recirculation system can comprise a recirculation supply tube that can be separate from a recirculation return tube. The tangential flow filtration input supply tube further can comprise at least one additional inlet hole disposed along the length of the tangential flow filtration input supply tube. The recirculation supply tube further can comprise at least one additional inlet hole disposed along the length of the recirculation supply tube. The input composition can fill the storage vessel to a desired storage vessel fill height.

In certain embodiments, the retentate return tube and/or recirculation return tube can selectively terminate in the interior of the storage vessel above or below the storage vessel fill height; in the interior of the storage vessel proximate a bottom of the storage vessel and/or can be directed towards a side in the interior of the storage vessel.

The tangential flow filtration (TFF) system and tangential flow filtration (TFF) module can be configured to retain and filter a viscous composition without a substantial concentration gradient in the viscous composition. The input composition can fill the storage vessel to a desired storage vessel fill height. The storage vessel cap seals aseptically to the top of the storage vessel, and can be made of at least one of a pharmaceutical grade material and a medical device grade material. The medical device grade material can comprise at least one of 316 stainless steel, silicone, ethylene propylene diene monomer, polypropylene, high density polyethylene, low density polyethylene and glass. The pharmaceutical grade material can comprise at least one of 316 stainless steel, silicone, ethylene propylene diene monomer, polypropylene, high density polyethylene, low density polyethylene and glass. The systems, apparatus, etc., can further comprise sanitary connections.

In certain aspects, the discussion herein comprises methods for the tangential flow filtration of an input composition. The methods can comprise:

providing the input composition in a storage vessel, the storage vessel having a top, a bottom, at least one side and an interior and the input composition filling the storage vessel to a desired storage vessel fill height;

providing a tangential flow filtration module;

extracting the input composition from different depths in the storage vessel;

subjecting the extracted input composition to tangential flow filtration to produce a tangential flow filtration retentate and a tangential flow filtration permeate; and returning the tangential flow filtration retentate to the interior of the storage vessel.

The methods can further comprise mixing the input composition in the storage vessel by extracting and returning the input composition from and to the storage vessel and/or mixing the tangential flow filtration retentate with a diafiltration solution before returning the tangential flow filtration retentate to the storage vessel. The mixing can occur proximate the tangential flow filtration module. The input composition can comprise providing a viscous composition such as a viscous solution, for example having a centipoise measure as discussed herein.

Returning the tangential flow retentate to the storage vessel can comprise returning the tangential flow filtration retentate and/or recirculation fluid to the interior of the storage vessel above or below the storage vessel fill height, to the interior of the storage vessel proximate the bottom of the storage vessel, and/or towards a side on the interior of the storage vessel. Mixing the input composition can comprise extracting the input composition from different depths within the storage vessel. Mixing the input composition can comprise returning the input composition to the interior of the storage vessel above the storage vessel fill height. Mixing the input composition can comprise returning the input composition to the interior of the storage vessel below the storage vessel fill height. Mixing the input composition can comprise returning the input composition to the interior of the storage vessel proximate the bottom of the storage vessel. Mixing the input composition can comprise directing the input composition towards a side on the interior of the storage vessel.

These and other aspects, features and embodiments are set forth within this application, including the following Detailed Description and attached drawings. Unless expressly stated otherwise, all embodiments, aspects, features, etc., can be mixed and matched, combined and permuted in any desired manner.

Figure 1A:
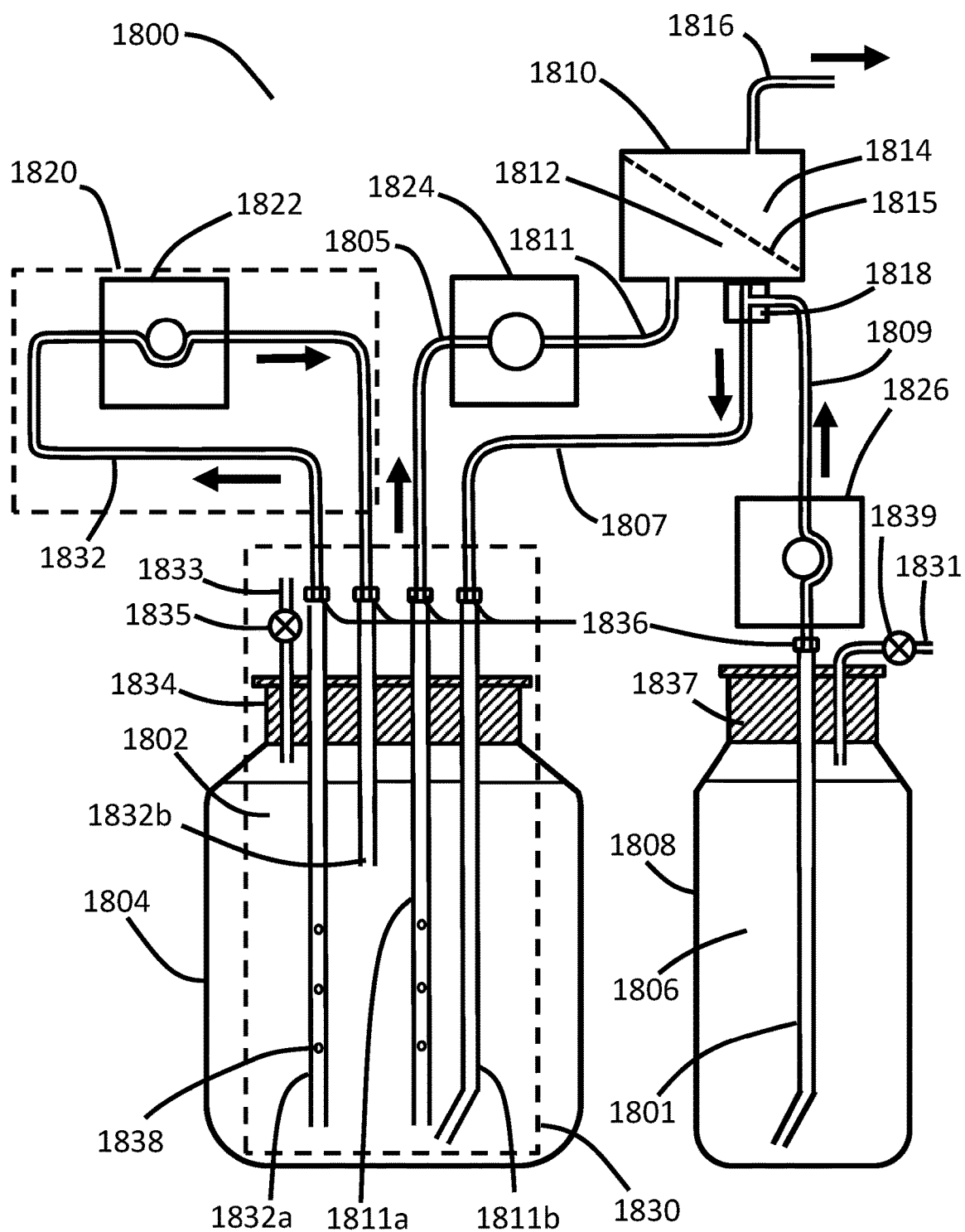
FIG. 1A schematically depicts an exemplary system for the tangential flow filtration (TFF) of input compositions, including avoiding or reducing concentration gradients between the top and bottom of the storage vessels.

The drawings, including the flow charts, present exemplary embodiments of the present disclosure. The drawings are not necessarily to scale and certain features may be exaggerated or otherwise represented in a manner to help illustrate and explain the present systems, methods, etc. Actual embodiments of the systems, methods, etc., herein may include further features or steps not shown in the drawings. The exemplifications set out herein illustrate embodiments of the systems, methods, etc., in one or more forms, and such exemplifications are not to be construed as limiting the scope of the disclosure in any manner. The embodiments herein are not exhaustive and do not limit the disclosure to the precise form disclosed, for example in the following detailed description.

DETAILED DESCRIPTION

Apparatus, methods, systems, etc., are provided for the tangential flow filtration (TFF) of input compositions, including viscous compositions, for example, viscous fluids, solutions, gels, pastes, creams and suspensions with viscosities greater than 10 cP, 20 cP, 50 cP or 100 cP. In TFF, an input composition flows alongside a filter membrane that filters out certain contents from that input composition. As noted above, anything that crosses the filter membrane is known as the "permeate" and anything that stays on the initial side of the membrane is known as the "retentate". TFF comprises continuous recirculation of the input composition along-side the filter membrane. The filter membrane can be contained in a housing such as a cassette or cartridge that is itself contained in a plate and frame system.

The apparatus, systems etc., herein provide effective and even aseptic mixing of the input composition in the storage tank, which helps reduce or avoid concentration gradients and therefore helps reduce or avoid pressure increases in the system, the likelihood of high pressure problems during the TFF, and also helps reduce or avoid build-up of large molecules on filter membrane pores that could clog the filter membrane. By reducing the clogging of the filter membrane, the resulting permeate flow rate is on average increased by between about 5% to 50%, for example by about 10%, about 20%, about 30% or about 40%, when compared to systems without the mixing systems herein. Such increased permeate flow rates result, for example, in lower processing times and more effective filtering of desired/undesired components in the input composition. The mixing herein can also improve the consistency of the TFF filtration as a result of the reduction in filter membrane clogging, because when the membrane pores are clogged the actual molecular weight cutoff of the TFF filter will be smaller than listed by the manufacturer.

While the systems, apparatus, methods, etc., herein apply to a wide range of input compositions including viscous compositions and other compositions that can suffer from unwanted top-to-bottom concentration gradients. The systems, etc., can be exemplified by an input composition comprising a high molecular weight fucan composition. The TFF processes herein comprise continuous recirculation of the input composition being processed through the TFF filter. The input composition is filtered by the TFF filter to produce a TFF retentate and a TFF permeate. The systems herein can be operated continuously, such that the produced TFF retentate is treated as an intermediate product of the system, and is processed by the system or a secondary TFF system until a desired level of undesired components have been removed.

The term "aseptic" and its derivatives, for example "aseptically", are used herein to describe the exclusion of undesired biological materials, living or dead. So, for example and as shown in certain of the Figures, if storage vessel cap 1834 seals aseptically to the open end of storage vessel 1804, then it means that essentially no biological materials can penetrate that seal from outside storage vessel 1804 or from outside of storage vessel cap 1834 to contaminate the interior of storage vessel 1804.

The system in FIG. 1A depicts an exemplary system for tangential flow filtration (TFF) of input compositions including viscous compositions, comprising enhanced, aseptic mixing. In FIG. 1A, tangential flow filtration system (TFF system) 1800 mixes the input composition 1802, which can be a viscous composition, that is going to be filtered during the TFF. FIG. 1A is drawn schematically and not to scale. Components of TFF system 1800 in the embodiment depicted in FIG. 1A include storage vessel 1804, which contains the input composition 1802, and TFF module 1810, which holds the TFF filter 1815 and thus is the location where the TFF filtering takes place. Components of TFF system 1800 also include recirculation system 1820, which recirculates the contents of the storage vessel 1804. In particular, recirculation system 1820 mixes the contents of the storage vessel 1804 to reduce or avoid concentration gradients; such mixing can be separate from or in combination with mixing that may occur due to returning the TFF retentate 1812 from TFF module 1810 to storage vessel 1804. TFF system 1800 also comprises diafiltration solution vessel 1808, which holds diafiltration solution 1806 that is used to replenish solvent from input composition 1802 that crosses through TFF filter 1815 and thus is then extracted via TFF permeate (output) line 1816.

TFF system 1800 in the exemplary embodiment depicted also comprises recirculation pump 1822, TFF input pump 1824 and diafiltration solution input pump 1826, along with recirculation tube 1832, TFF input supply line 1805, TFF retentate return tube 1807, diafiltration solution supply line 1809, and TFF permeate line 1816, which carries the filtered output away from TFF module 1810 and out of TFF system 1800. Within TFF module 1810, TFF filter 1815 is schematically shown filtering the input composition 1802 and therefore creating TFF retentate 1812, which contains matter too large to cross TFF filter 1815, and TFF permeate 1814, which contains matter small enough to cross TFF filter 1815. TFF permeate 1814 is then carried out of the system by TFF permeate line 1816, and in FIG. 1A TFF permeate 1814 is shown departing the TFF system 1800 by TFF permeate line 1816.

Returning to diafiltration solution vessel 1808, it holds diafiltration solution 1806, which is used replenish solvent lost during the actual filtering process. In the embodiment shown, diafiltration solution vessel 1808 contains diafiltration solution supply tube 1801 that extends through diafiltration solution vessel cap 1837, that seals typically aseptically to diafiltration solution vessel 1808, to the bottom of the container, i.e., to proximate the base of diafiltration solution vessel 1808, in order to collect diafiltration solution 1806. The end of the diafiltration solution supply tube 1801 is operably connected to diafiltration solution supply line 1809 via a sanitary connector 1836. Diafiltration solution supply line 1809 supplies the diafiltration solution 1806 to tangential flow filtration retentate return tube 1807 and, in turn, storage vessel 1804 to replenish solvent lost during the actual filtering process.

The pumps, tubing and other components of the systems and apparatus herein can be any suitable pumps, tubing, containers, etc. For example, recirculation pump 1822 and diafiltration solution input pump 1826 may be peristaltic pumps, and TFF input pump 1824 may be a diaphragm pump. In FIG. 1A, the arrows show the direction of flow under the action of the various pumps.

Turning to Y-connector 1818 in the retentate return portion of the system, it connects the diafiltration solution vessel 1808 to the tangential flow filtration retentate return tube 1807. Placing Y-connector 1818 between the TFF module 1810 and the TFF retentate return tube 1807 (i.e., proximate the TFF module 1810) enhances the ability of diafiltration solution 1806 to mix with the TFF retentate 1812 on its way back to storage vessel 1804. In other embodiments, Y-connector 1818 can be placed along the TFF retentate return tube 1807 or even into storage vessel cap 1834. Providing diafiltration solution 1806 is helpful because the loss of solvent from the input composition 1802 into the TFF permeate 1814 increases the viscosity of the TFF retentate 1812 compared to the contents of storage vessel 1804. The mixing of diafiltration solution 1806 with the TFF retentate 1812 via Y-connector 1818 helps lower the viscosity of TFF retentate 1812 before it reaches storage vessel 1804 and consequently helps counter build-up of concentration gradient. Thus, placing the Y-connector 1818 near to the TFF module 1810 helps reduce concentration gradients in the contents of storage vessel 1804.

Turning to the mixing head 1830 on storage vessel 1804, in the embodiment shown in FIG. 1A, it has four ports. Mixing head 1830 comprises storage vessel cap 1834 that seals, typically aseptically, to storage vessel 1804. Mixing head 1830 may be manufactured from any suitable material such as a pharmaceutical grade or medical device grade material, for example, 316 stainless steel, silicone, ethylene propylene diene monomer, polypropylene, high density polyethylene, low density polyethylene, glass or other material that meets the sanitary standards of medical/pharmaceutical equipment.

In the embodiment shown, four tubes extend through storage vessel cap 1834 and are arranged to transmit fluid to and from storage vessel 1804. As shown by recirculation tube inlet 1832a, tangential flow filtration input tube inlet 1811a and tangential flow filtration retentate tube outlet 1811b, if desired the inlets and/or outlets can be disposed at different heights within storage vessel 1804, and therefore within input composition 1802 when the vessel is filled. Such arrangement encourages the mixing of the input composition 1802 within storage vessel 1804 and thus lessens or avoids concentration gradients and other potentially problematic build-up, etc. Adding, circulating or otherwise transmitting input composition through the tubes mixes the contents of the storage vessel 1804, thereby reducing problems at the TFF filter including by reducing concentration gradients in storage vessel 1804.

Turning to the tubes entering storage vessel 1804, recirculation tube 1832 comprises recirculation tube inlet 1832a and recirculation tube outlet 1832b. Recirculation tube inlet 1832a and recirculation tube outlet 1832b can be disposed at any desired height or level within the storage vessel 1804, provided that the flow within storage vessel stirs or otherwise mixes the input composition 1802 to significantly reduce, or even eliminate, concentration gradients within input composition 1802. Recirculation tube inlet 1832a is disposed at a level to extract input composition 1802, typically below the height which input composition 1802 fills storage vessel 1804 to (hereafter referred to as the "storage vessel fill height"), i.e., into the body of input composition 1802. Recirculation tube inlet 1832a and recirculation tube outlet 1832b can be disposed at different heights within input composition 1802 such that, if there is a concentration gradient within the input composition 1802 then the inlet and outlet cooperate to transport one concentration level into another, thereby mixing the concentration gradients. Other approaches to such mixing can also, or alternatively, be used, for example the incoming stream can be directed against a side of the storage vessel 1804, causing circulation and even a vortex if desired.

Figure 1B:
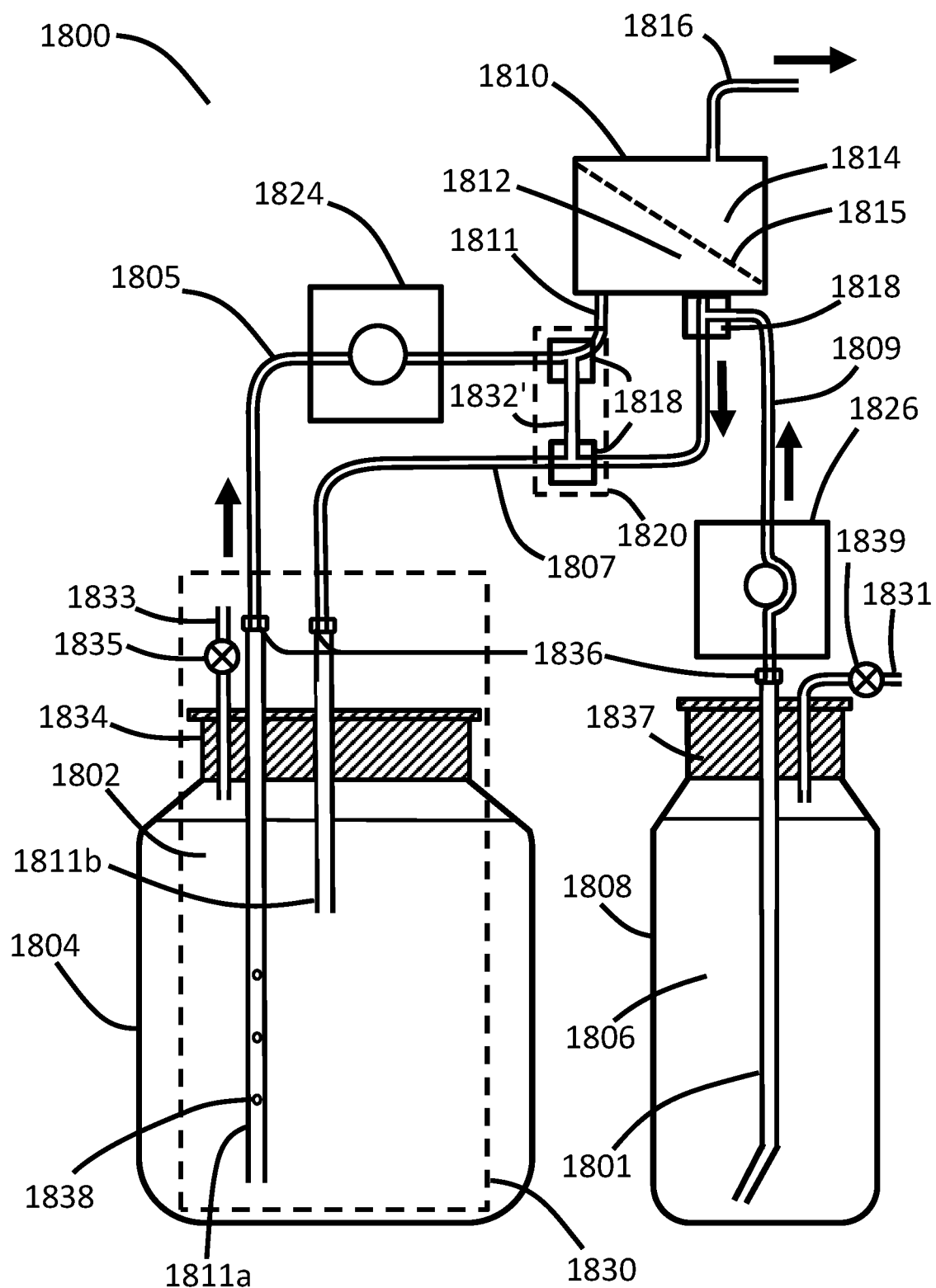
FIG. 1B schematically depicts another exemplary system for the tangential flow filtration (TFF) of input compositions, including avoiding or reducing concentration gradients between the top and bottom of the storage vessels.

Next, at least one TFF input supply tube 1811 transfers input composition 1802 from storage vessel 1804 to tangential flow filtration (TFF) module 1810 and then returns the TFF retentate 1812 to storage vessel 1804. As with the other tubes herein, they can be unitary or, as depicted in FIG. 1A, it can comprise multiple components including pumps, valves, different materials for different portions of the tubes, etc. In the embodiment in FIG. 1A, TFF input tube inlet 1811a extracts input composition 1802 from storage vessel 1804 and transfers it via TFF input pump 1824 to TFF module 1810. In the embodiment in FIG. 1A, TFF input tube inlet 1811a comprises multiple inlet ports 1838 disposed along its length at different depths below the storage vessel fill height. In some embodiments, as exemplified in FIG. 1B, the tangential flow filtration input supply tube 1811 is configured to extract input composition from the storage vessel 1804 and deliver the input composition to both the tangential flow filtration module 1810 and the recirculation system 1820 via, for example, a Y-connector 1818. In the embodiment in FIG. 1B, recirculation return tube 1832' connects to TFF retentate return tube 1807 such that retentate returning to the storage vessel 1804 are transported into the storage vessel 1804 via a single tube through storage vessel cap 1834. Thus, in the embodiment shown, the composition in the recirculation system 1820 joins the TFF retentate 1812 at the TFF retentate return tube 1807 via recirculation return tube 1832', which connection is upstream from storage vessel 1804 and can be, for example, a Y-connector 1818. The combined recirculation composition and TFF retentate 1812 is then delivered back into storage vessel 1804. In other words, as shown by the embodiments in FIGS. 1A and 1B, the extraction tube(s) and/or the return tube(s) for each of the recirculation system 1820 and the TFF module 1810 can each be a single shared tube, can be separate tubes, or otherwise as desired.

Figure 1C:
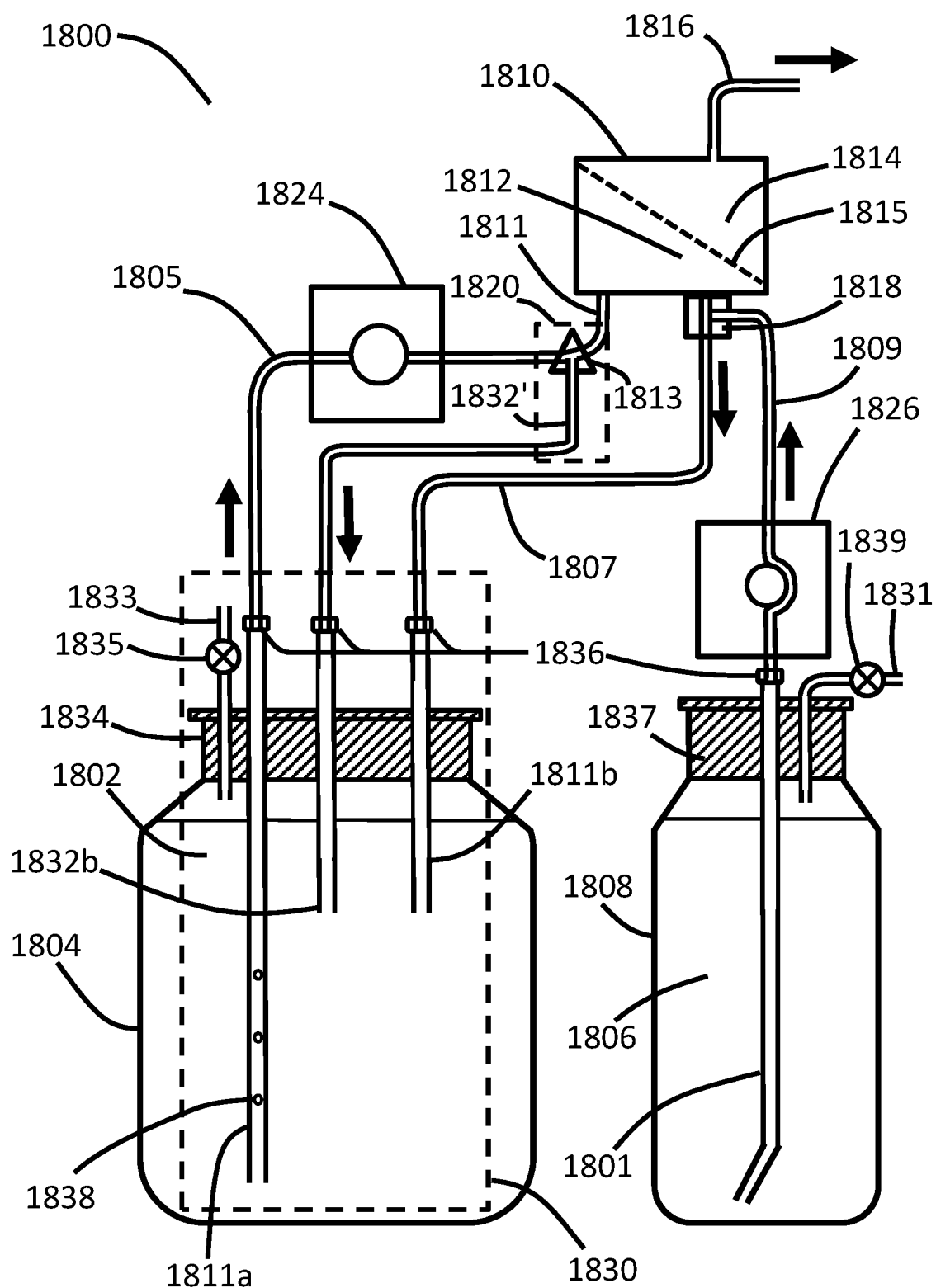
FIG. 1C schematically depicts another exemplary system for the tangential flow filtration (TFF) of input compositions, including avoiding or reducing concentration gradients between the top and bottom of the storage vessels.

In FIG. 1C, recirculation return tube 1832' connects to recirculation tube outlet 1832b so that the composition in the recirculation system 1820 is returned to the storage vessel 1804 without first passing through TFF module 1810. In some embodiments, including the embodiment in FIG. 1C, a pressure bypass valve 1813 can be provided in the tangential flow filtration input supply tube 1811. The pressure bypass valve 1813 can be set at a pressure less than the upper pressure limit for TFF module 1810 so that the chance of pressure-caused problems or failures in TFF module 1810 is reduced or eliminated. In addition, if desired, the output pressure of TFF input pump 1824 can be set higher than the level for pressure bypass valve 1813, to assure that a portion of input composition 1802 is recirculated through the recirculation system 1820 without passing through TFF module 1810; the portion or percentage that is recirculated without TFF can be set at a specific and/or predetermined level if desired. Such a configuration provides for both TFF and recirculation with only a single pump, and also enhances the effectiveness and durability of TFF module 1810 because it reduces or eliminates over-pressure problems while also reducing or eliminating concentration gradients within input composition 1802.

Turning to a further discussion of certain aspects or embodiments depicted in FIG. 1A, in the embodiment shown, recirculation tube inlet 1832a extends to the bottom of storage vessel 1804, i.e., to proximate the base of storage vessel 1804. Recirculation tube inlet 1832a gathers input composition 1802 from storage vessel 1804, in FIG. 1A, from the bottom of storage vessel 1804. The input composition extracted can be propelled in any desired manner, for example by a recirculation pump 1822. Recirculation tube inlet 1832a may have a plurality of further inlet ports 1838 disposed along its length at different depths below the storage vessel fill height. For the sake of clarity, only one inlet port 1838 is numbered in FIG. 1A. Inlet ports 1838, if present, allows recirculation tube inlet 1832a to draw input composition 1802 simultaneously from different depths below the storage vessel fill height. This serves to counter any vertical concentration gradient in the input composition 1802 in storage vessel 1804. The distal end of recirculation tube inlet 1832a outside storage vessel 1804 can be connected aseptically with the end of recirculation tube 1832 via a sanitary connector 1836.

Recirculation tube outlet 1832b is disposed to return any composition pumped through recirculation pump 1822 to storage vessel 1804. The end of recirculation tube outlet 1832b outside storage vessel 1804 is connected aseptically with the return segment of recirculation tube 1832 via a sanitary connector 1836. Recirculation tube outlet 1832b may be terminated above the storage vessel fill height so that portions of the input composition 1802 that have higher density than the rest will be assisted by the flow of the incoming stream and by gravity in distributing downward through storage vessel 1804, facilitating thereby the mixing of input composition 1802 in storage vessel 1804. Recirculation tube outlet 1832b may also be terminated below the storage vessel fill height so that the turbulence of the flow assists with the mixing of the contents of the input composition 1802, or so that the returning stream is deflected off the base of storage vessel 1804 to facilitate mixing. In some embodiments, recirculation tube outlet 1832b is bent to specifically direct the incoming stream towards the side of the storage vessel 1804 to facilitate mixing in a circular motion.

TFF input tube inlet 1811a extends to the bottom of storage vessel 1804. TFF input tube inlet 1811a has a plurality of further inlet ports 1838 disposed along the length of TFF input tube inlet 1811a at different depths below the storage vessel fill height. This allows TFF input tube inlet 1811a to draw input composition 1802 simultaneously from different depths below the storage vessel fill height, which helps counter any vertical concentration gradient in the input composition 1802 in storage vessel 1804. The outside end of TFF input tube inlet 1811a can be connected aseptically with TFF input supply line 1805 via a sanitary connector 1836.

The diafiltration solution 1806 is fed directly into the TFF retentate 1812 through a Y connector 1818, diluting the more viscous TFF retentate 1812 with the diafiltration solution before it returns to storage vessel 1804 through TFF retentate tube outlet 1811b. TFF retentate tube outlet 1811b may be terminated above the storage vessel height so that portions of the mixed TFF retentate-diafiltration solution that have higher density will be assisted by the flow of the incoming stream and by gravity to distribute downward through storage vessel 1804, thereby facilitating the mixing of the incoming stream with in the contents of storage vessel 1804. TFF retentate tube outlet 1811b may be terminated below the storage vessel fill height so that the turbulence of the flow assists with the mixing of the contents, and can also be configured, as shown in FIG. 1A, so that the returning stream is deflected off the base of storage vessel 1804 to facilitate mixing. In some embodiments, TFF retentate tube outlet 1811b is bent to specifically direct the incoming stream towards the side of the storage vessel 1804 to facilitate mixing in a circular motion. The outside end of TFF retentate tube outlet 1811b can be connected aseptically with TFF retentate return tube 1807 via a sanitary connector 1836. The four tubes discussed above can also be joined or otherwise configured so that there are more or less than four tubes entering/exiting storage vessel 1804. For example, tubes 1832b and 1811b can be fluidly connected before entering storage vessel cap 1834 and/or storage vessel 1804.

Mixing head 1830 may also comprise additional ports and tubes, for example a vent port 1833 with a suitable vent port valve 1835 to be opened as desired to relieve air or gas pressure in storage vessel 1804. The vent port 1833 may be fitted with an appropriate vent filter (not shown) to further prevent to contamination of the contents of storage vessel 1804. In FIG. 1A, the various tubes are shown in a line. The tubes can be disposed in a row, a circle or otherwise as desired.

Diafiltration solution vessel cap 1837 on diafiltration solution vessel 1808 may also comprise additional elements, for example a vent port 1831 with a suitable vent port valve 1839 to be opened when desired to relieve air or gas pressure in diafiltration solution vessel 1808. The vent port 1831 may be fitted with an appropriate vent filter (not shown) to further prevent to contamination of the diafiltration solution.

The TFF system 1800 disclosed herein may be described in more general terms as a system for TFF of input compositions including viscous compositions, the TFF system 1800 comprising: a TFF module 1810; a first storage vessel 1804 having a bottom, a top, at least one side and an interior; a storage vessel cap 1834 arranged, typically, to aseptically seal the open end of the first storage vessel 1804; a TFF input tube inlet 1811a for extracting input composition 1802 from the storage vessel 1804 and sending such input composition to the TFF module 1810, the TFF input tube inlet 1811a extending through the storage vessel cap 1834 into the interior of the storage vessel 1804 to proximate the lower closed end of the storage vessel 1804, the TFF input tube inlet 1811a can comprise a plurality of inlet ports 1838 disposed at different depths below the storage vessel fill height; and a TFF retentate tube outlet 1811b extending through the storage vessel cap 1834 to terminate in the interior of the storage vessel 1804 for returning the TFF retentate 1812 to the storage vessel 1804. The contents in the storage vessel 1804 can have a predetermined storage vessel fill height.

The TFF system 1800 may further comprise a recirculation system 1820. The recirculation system 1820 can, in some embodiments, comprise a recirculation tube inlet 1832a extending through the storage vessel cap 1834 into the interior of the storage vessel 1804 to proximate the lower closed end of the storage vessel 1804 for extracting the input composition 1802 from the storage vessel 1804, the recirculation tube inlet 1832a can comprise a plurality of inlet ports 1838 disposed at different depths below the storage vessel fill height; a recirculation tube outlet 1832b extending through the storage vessel cap 1834 to terminate in the interior of the storage vessel 1804; a recirculation pump 1822 disposed to circulate the input composition 1802 via the recirculation tube inlet 1832a from the storage vessel 1804 and along a recirculation tube 1832 back to the storage vessel 1804 via the recirculation tube outlet 1832b. The recirculation tube inlet 1832a and recirculation tube outlet 1832b may be aseptically connected to the recirculation tube 1832 by, for example, sanitary connectors 1836. The recirculation system 1820 can be operated continuously, such that the contents of storage vessel 1804 being further processed by TFF system 1800 is simultaneously supplied to the recirculation system 1820.

The TFF system 1800 may further comprise a TFF input pump 1824 disposed to supply input composition 1802 via the TFF input tube inlet 1811a from the storage vessel 1804 and along a TFF input supply line 1805 to the TFF module 1810 and back from the TFF module 1810 to the storage vessel 1804 along a TFF retentate return tube 1807 via the TFF retentate tube outlet 1811b. The TFF input tube inlet 1811a may be connected aseptically to the TFF input supply line 1805 by a sanitary connector 1836 and the TFF retentate tube outlet 1811b may be connected aseptically to the TFF retentate return tube 1807 by a sanitary connector 1836.

The TFF system 1800 may further comprise: a second diafiltration solution vessel 1808 for holding diafiltration solution 1806, the diafiltration solution vessel 1808 having a closed base, an upper open end and an interior; an diafiltration solution vessel cap 1837 arranged to aseptically seal the open end of the diafiltration solution vessel 1808; a diafiltration solution supply tube 1801 extending through the diafiltration solution vessel cap 1837 into the interior of the diafiltration solution vessel 1808 to proximate the base of the diafiltration solution vessel 1808; a diafiltration solution supply line 1809 aseptically joining the diafiltration solution supply tube 1801 to the TFF retentate return tube 1807, wherein the diafiltration solution supply line 1809 is in some embodiments aseptically connected to the TFF retentate return tube 1807 proximate the TFF module 1810; and a third diafiltration solution input pump 1826 for pumping diafiltration solution 1806 through the diafiltration solution supply tube 1801 along the diafiltration solution supply line 1809 to the TFF retentate return tube 1807. The diafiltration solution supply line 1809 may be aseptically connected to the diafiltration solution supply tube 1801 by, for example, a sanitary connector 1836 and the diafiltration solution supply line 1809 may be connected to the TFF retentate return tube 1807 by, for example, a sanitary Y-connector 1818.

The TFF system 1800 may be operated for a predetermined or other desired amount of time, or the level of undesired components in the contents of storage vessel 1804 can be measured and the operation continued until the level of undesired components has dropped below a predetermined or other desired level.

Figure 2:
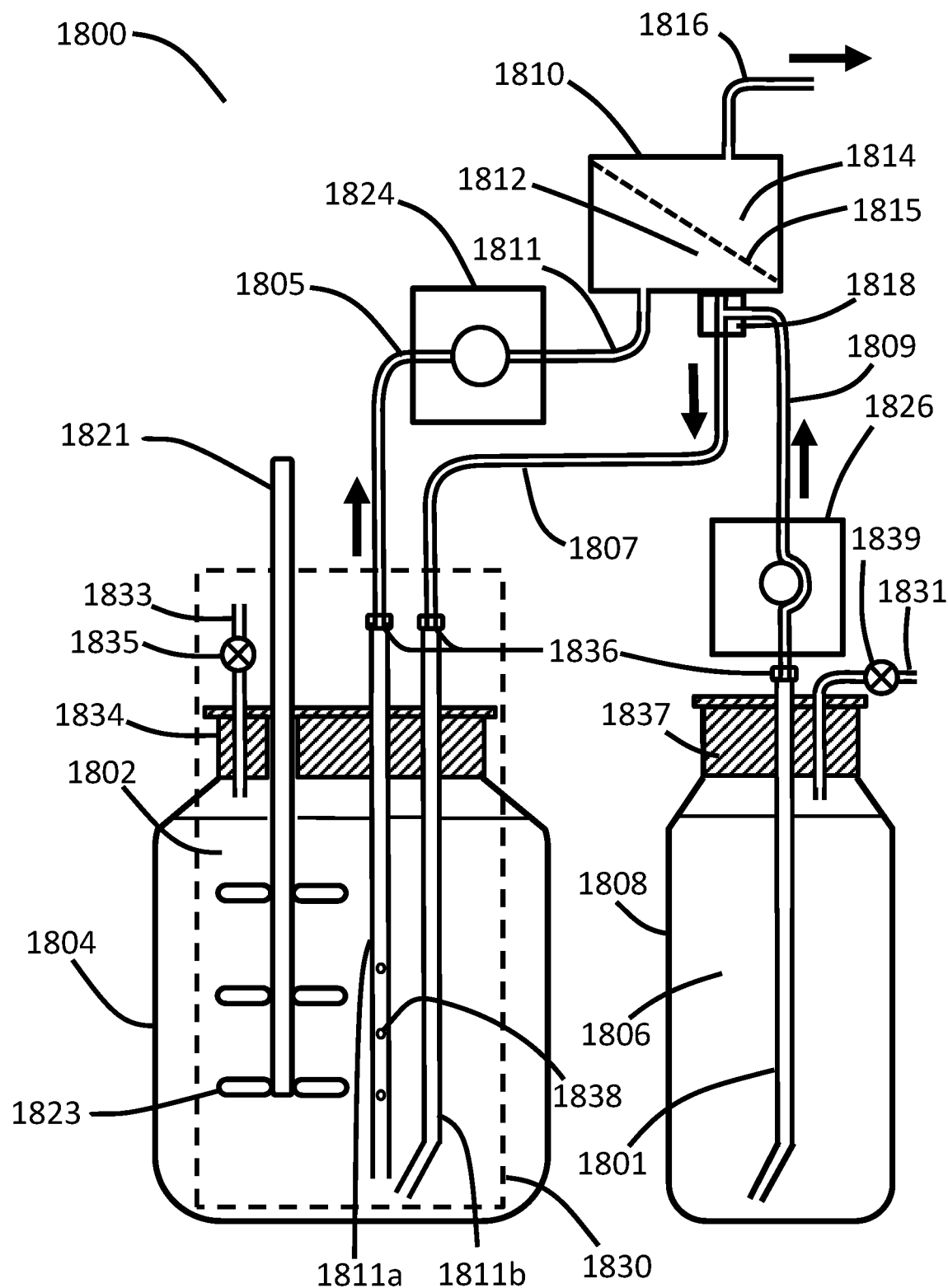
FIG. 2 schematically depicts another exemplary systems for the tangential flow filtration (TFF) of input compositions, including avoiding or reducing concentration gradients between the top and bottom of the storage vessels.

Another embodiment of a system for TFF of input compositions including viscous compositions is shown in FIG. 2. In FIG. 2, the recirculation system 1820, including the recirculation pump 1822, the recirculation tube 1832, the recirculation tube inlet 1832a and the recirculation tube outlet 1832b of FIG. 1A, have been replaced with mixing propeller 1821 equipped with at least one mixing propeller blade 1823. Mixing propeller blade 1823 can be any desired, suitable shape and can be disposed at any desired, suitable position along the mixing propeller 1821. In the embodiment shown, mixing propeller 1821 extends through storage vessel cap 1834 and terminates under the storage vessel fill height, but the entire mixing propeller system can, if desired, be located within storage vessel 1804. An appropriate device (not shown) such as a motor configured to rotate the mixing propeller 1821 at a desired speed can be used to rotate the mixing propeller 1821, thus mixing the input composition 1802 in storage vessel 1804 and thereby countering any concentration gradient present in storage vessel 1804.

Figure 3:
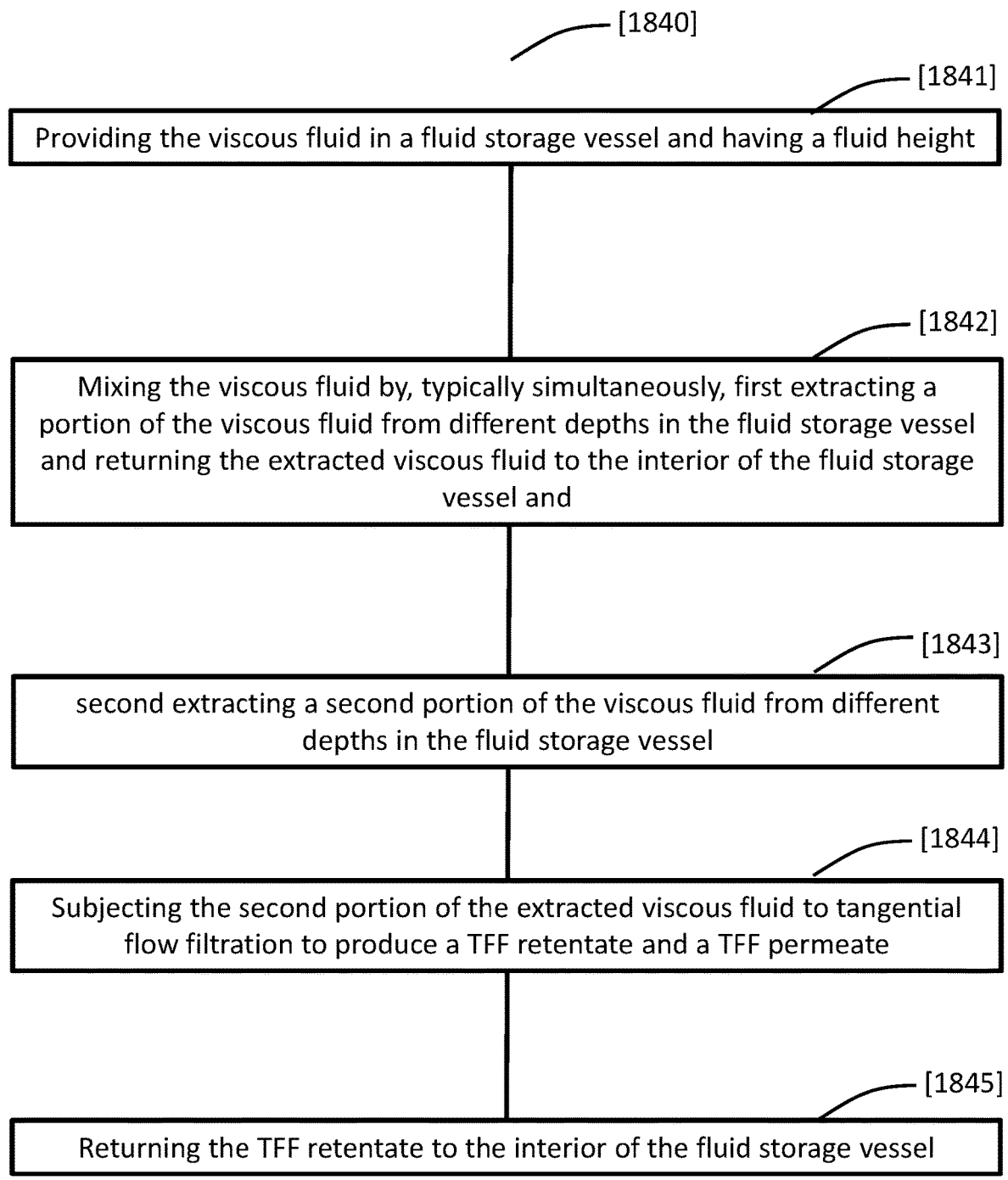
FIG. 3 depicts a flow chart of an exemplary method for the TFF of input compositions, including avoiding or reducing concentration gradients between the top and bottom of the storage vessels.

Next, the flow chart of FIG. 3 depicts an exemplary method [1840] for TFF of an input composition 1802 using systems as discussed herein, for example as exemplified in FIG. 1A, the method comprising: providing [1841] the input composition 1802 in a storage vessel 1804 such that the input composition 1802 fills the storage vessel 1804 to a storage vessel fill height; mixing [1842] the input composition 1802 by, typically simultaneously, first extracting a portion of the input composition 1802 from different depths in the storage vessel 1804 and returning the extracted input composition 1802 to the interior of the storage vessel 1804, and second extracting [1843] a second portion of the input composition 1802 from different depths in the storage vessel 1804. The second portion of the extracted input composition 1802 is then subjected [1844] to TFF to produce a TFF retentate 1812 and a TFF permeate 1814. The TFF retentate 1812 is then returned [1845] to the interior of the storage vessel 1804.

The methods [1840] may further comprise providing a diafiltration solution 1806 in a diafiltration solution vessel 1808 and mixing the diafiltration solution 1806 with the TFF retentate 1812 before the returning [1845] the TFF retentate 1812 to the interior of the storage vessel 1804. Returning [1845] the TFF retentate 1812 to the interior of the storage vessel 1804 may comprise directing the returning TFF retentate 1812 to the closed bottom end of the first storage vessel 1804. Returning [1845] the TFF retentate 1812 to the interior of the storage vessel 1804 may comprise directing the returning TFF retentate 1812 to above the storage vessel fill height. Returning [1845] the TFF retentate 1812 to the interior of the storage vessel 1804 may comprise directing the returning TFF retentate 1812 to below the storage vessel fill height. Returning [1845] the TFF retentate 1812 to the interior of the storage vessel 1804 may comprise directing the returning TFF retentate 1812 towards the side of the storage vessel 1804 to facilitate mixing in a circular motion.

Figure 4:
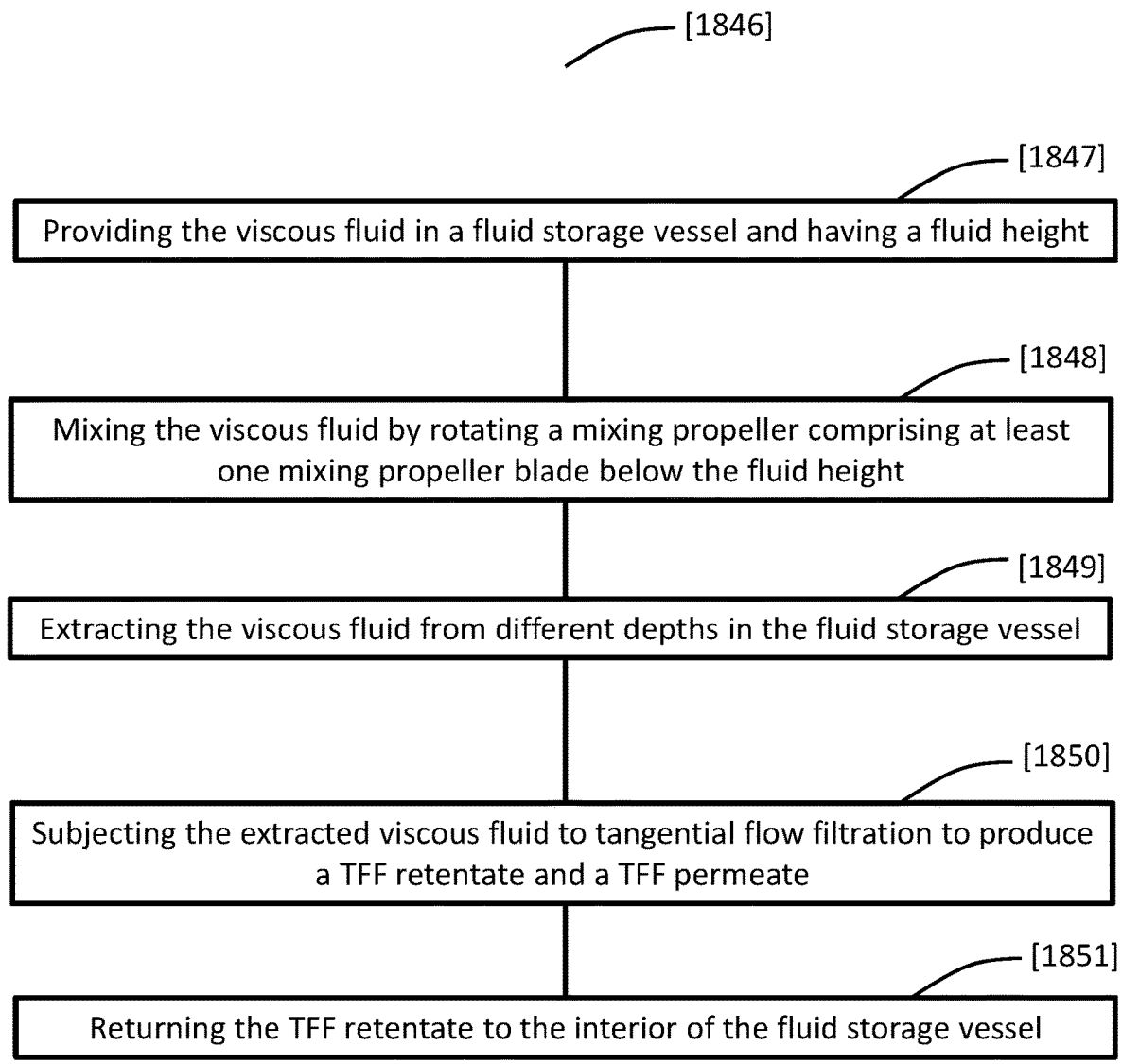
FIG. 4 depicts another flow chart of an exemplary method for the TFF of input compositions, including avoiding or reducing concentration gradients between the top and bottom of the storage vessels.

The flow chart of FIG. 4 depicts another exemplary method [1846] for TFF of an input composition 1802 using systems exemplified in FIG. 2, the method comprising: providing [1847] the input composition 1802 in a storage vessel 1804 such that the input composition 1802 fills the storage vessel 1804 to a storage vessel fill height; mixing [1848] the input composition 1802 by rotating a mixing propeller 1821 comprising at least one mixing propeller blade 1823 below the storage vessel fill height; and extracting [1849] the input composition 1802 from different depths in the storage vessel 1804. The extracted input composition 1802 is then subjected [1850] to TFF to produce a TFF retentate 1812 and a TFF permeate 1814. The TFF retentate 1812 is then returned [1851] to the interior of the storage vessel 1804.

The methods [1846] may further comprise providing a diafiltration solution 1806 in a diafiltration solution vessel 1808 and mixing the diafiltration solution 1806 with the TFF retentate 1812 before the returning [1851] the TFF retentate 1812 to the storage vessel 1804.

By using the TFF systems and methods herein, an operator can accomplish effective mixing of a highly viscous composition while maintaining aseptic conditions and procedures throughout the processing of the bulk composition. To this end, any line in the process may be spliced to incorporate a sampling port. The sampling port may be in the form of, for example, a 3-way valve.

EXAMPLES

Example 1: Use of TFF System with a Viscous Fucoidan Solution

The system shown in FIG. 1A was tested with a fucoidan solution of viscosity greater than 50 cP, but not exceeding 120 cP. The recirculation pump 1822 was set at a flow rate of about 3.2 liters/min. The diafiltration solution input pump 1826 was set to match the TFF permeate 1814 flow rate, measured at TFF permeate line 1816. The TFF input pump 1824 was set to accomplish a trans-membrane pressure of between 10 psi and 40 psi, for example about 15 psi, 20 psi, 25 psi, 30 psi and 35 psi. this keeps the pressure below levels that often cause failure; fluid pumps can usually handle about 60-80 psi while the tubing can usually handle about 40 psi.

Processing of the viscous fucoidan solution without the apparatus and systems herein resulted in an observation of a significant, harmful concentration gradient in the storage vessel 1804 from the returning of TFF retentate 1812 to storage vessel 1804. Low permeate flux (rate of flow of permeate through the membrane of the TFF module) was seen, indicating that the filter membrane was getting clogged. Upon incorporation of systems herein, the concentration gradient was no longer observed in the storage vessel 1804 and the average permeate flux was about 20% higher than observed when using conventional TFF apparatus without a recirculation system 1820, Y-connector 1818 or tubes configured to pick-up and return fluid from and to different locations in the storage vessel 1804.

The present application is further directed to compositions made according to the various elements of the apparatus, methods, systems, etc., discussed herein as well as to methods of using the compositions and to systems and devices configured to perform the methods herein and obtain desired low bioburden, viscous medical devices, combination products and pharmaceuticals.

REFERENCE NUMERAL LIST

1800 Tangential flow filtration (TFF) system
1801 Diafiltration solution supply tube
1802 Input composition
1804 Storage vessel
1805 TFF input supply line
1806 Diafiltration solution
1807 Tangential flow filtration retentate return tube
1808 Diafiltration solution vessel
1809 Diafiltration solution supply line
1810 Tangential flow filtration module
1811 Tangential flow filtration input supply tube
1811a Tangential flow filtration input tube inlet
1811b Tangential flow filtration retentate tube outlet
1812 Tangential flow filtration retentate
1813 Pressure bypass valve
1814 Tangential flow filtration permeate
1815 Tangential flow filtration filter
1816 Tangential flow filtration permeate line
1818 Y-connector
1820 Recirculation system
1821 Mixing propeller
1822 Recirculation Pump
1823 Mixing propeller blade
1824 Tangential flow filtration input pump
1826 Diafiltration solution input pump
1830 Mixing head
1831 Vent port
1832 Recirculation tube
1832' Recirculation return tube
1832a Recirculation tube inlet
1832b Recirculation tube outlet
1833 Vent port
1834 Storage vessel cap
1835 Vent port valve
1836 Sanitary connector(s)
1837 Diafiltration solution vessel cap
1838 Inlet port(s)
1839 Vent port valve
1840 A method for tangential flow filtration of an input composition
1841 Providing the input composition in a storage vessel such that the input composition fills the storage vessel to a storage vessel fill height
1842 Mixing the input composition by, typically simultaneously, first extracting a portion of the input composition from different depths in the storage vessel and returning the extracted input composition to the interior of the storage vessel and
1843 second extracting a second portion of the input composition from different depths in the storage vessel
1844 Subjecting the second portion of the extracted input composition to tangential flow filtration to produce a TFF retentate and a TFF permeate
1845 Returning the TFF retentate to the interior of the storage vessel
1846 A method for tangential flow filtration of an input composition
1847 Providing the input composition in a storage vessel such that the input composition fills the storage vessel to a storage vessel fill height
1848 Mixing the input composition by rotating a mixing propeller comprising at least one mixing propeller blade below the storage vessel fill height
1849 Extracting the input composition from different depths in the storage vessel
1850 Subjecting the extracted input composition to tangential flow filtration to produce a TFF retentate and a TFF permeate
1851 Returning the TFF retentate to the interior of the storage vessel All terms used herein are used in accordance with their ordinary meanings unless the context or definition clearly indicates otherwise. Also, unless expressly indicated otherwise, in the specification the use of "or" includes "and" and vice-versa. Non-limiting terms are not to be construed as limiting unless expressly stated, or the context clearly indicates, otherwise (for example, "including," "having," and "comprising" typically indicate "including without limitation"). Singular forms, including in the claims, such as "a," "an," and "the" include the plural reference unless expressly stated, or the context clearly indicates, otherwise.

Unless otherwise stated, adjectives herein such as "substantially" and "about" that modify a condition or relationship characteristic of a feature or features of an embodiment, indicate that the condition or characteristic is defined to within tolerances that are acceptable for operation of the embodiment for an application for which it is intended.

The scope of the present methods, compositions, systems, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

From the foregoing, it will be appreciated that, although specific embodiments have been discussed herein for purposes of illustration, various modifications may be made without deviating from the spirit and scope of the discussion herein. Accordingly, the systems and methods, etc., include such modifications as well as all permutations and combinations of the subject matter set forth herein and are not limited except as by the appended claims or other claim having adequate support in the discussion and figures herein.

What is claimed is:

1. A tangential flow filtration system comprising:
   a tangential flow filtration module;
   a storage vessel comprising an input composition;
   a tangential flow filtration input supply tube configured to deliver input composition from multiple depths within the storage vessel to the tangential flow filtration module, wherein the tangential flow filtration input supply tube comprises a plurality of inlet ports disposed at different heights within the storage vessel; and
   a retentate return tube configured to return TFF retentate from the tangential flow filtration module to the storage vessel.

2. The tangential flow filtration system of claim 1 further comprising a recirculation system separate from the tangential flow filtration module and comprising a recirculation tube having a recirculation tube inlet disposed within the storage vessel at a depth selected to extract contents of the storage vessel and having a recirculation tube outlet disposed inside the storage vessel, wherein the recirculation system is configured such that anything in the recirculation system does not pass through the tangential flow filtration module and wherein the recirculation tube inlet and the recirculation tube outlet are located within in the storage vessel such that passage of the contents of the storage vessel through the recirculation system inhibits concentration gradients within the storage vessel.

3. A tangential flow filtration (TFF) system comprising:
   a tangential flow filtration (TFF) module;
   a storage vessel comprising an input composition;
   a tangential flow filtration input supply tube operably connected to deliver input composition from the storage vessel to the tangential flow filtration module; and
   a retentate return tube operably connected to return TFF retentate from the tangential flow filtration module to the storage vessel;
   wherein the TFF system further comprises:
   a recirculation system separate from the tangential flow filtration module and comprising a recirculation tube having a recirculation tube inlet comprising at least one additional inlet hole disposed along the length of a recirculation supply tube disposed within the storage vessel at a depth selected to extract contents of the storage vessel and having a recirculation tube outlet disposed inside the storage vessel, wherein the recirculation system is configured such that anything in the recirculation system does not pass through the tangential flow filtration module and wherein the recirculation tube inlet and the recirculation tube outlet are located within in the storage vessel such that passage of the contents of the storage vessel through the recirculation system inhibits concentration gradients within the storage vessel.

4. The tangential flow filtration system of any one of claim 2 or 3 wherein the recirculation system further comprises a recirculation system pump disposed to pump the contents of the storage vessel through the recirculation system, the recirculation system pump not connected to the tangential flow filtration module.

5. The tangential flow filtration system of any of claim 2 or 3 wherein the tangential flow filtration supply tube and the retentate return tube terminate at different depths in the interior of the storage vessel.

6. The tangential flow filtration system of any one of claim 2 or 3 wherein the retentate return tube terminates in the interior of the storage vessel above the storage vessel fill height.

7. The tangential flow filtration system of any one of claim 2 or 3 wherein the retentate return tube terminates in the interior of the storage vessel below the storage vessel fill height.

8. The tangential flow filtration system of any one of claim 2 or 3 wherein the retentate return tube terminates in the interior of the storage vessel proximate a bottom of the storage vessel.

9. The tangential flow filtration system of any one of claim 2 or 3 wherein the retentate return tube is directed towards a side in the interior of the storage vessel.

10. The tangential flow filtration system of any one of claim 2 or 3 wherein the recirculation tube outlet terminates in the interior of the storage vessel above a storage vessel fill height.

11. The tangential flow filtration system of any one of claim 2 or 3 wherein the recirculation tube outlet terminates in the interior of the storage vessel below a storage vessel fill height.

12. The tangential flow filtration system of any one of claim 2 or 3 wherein the recirculation tube outlet terminates in the interior of the storage vessel proximate a bottom of the storage vessel.

13. The tangential flow filtration system of any one of claim 2 or 3 wherein the recirculation tube outlet is directed towards a side in the interior of the storage vessel.

14. The tangential flow filtration system of any of claim 2 or 3 further comprising a diafiltration solution supply tube configured to deliver diafiltration solution to the retentate return tube upstream from the storage vessel.

15. The tangential flow filtration system of any of claim 2 or 3 wherein the tangential flow filtration system and tangential flow filtration module are configured to retain and filter a viscous composition without a substantial concentration gradient in the viscous composition.

16. The tangential flow filtration system of any of claim 2 or 3 further comprising a storage vessel cap, wherein the tangential flow filtration input supply tube and the retentate return tube extend through the storage vessel cap into the interior of the storage vessel.

17. The tangential flow filtration system of claim 16 wherein the storage vessel cap seals aseptically to the top of the storage vessel.

18. A tangential flow filtration (TFF) system comprising:
 a tangential flow filtration (TFF) module;
 a storage vessel comprising an input composition;
 a tangential flow filtration input supply tube operably connected to deliver input composition from the storage vessel to the tangential flow filtration module; and
 a retentate return tube operably connected to return TFF retentate from the tangential flow filtration module to the storage vessel;

wherein the TFF system further comprises:
 a recirculation system separate from the tangential flow filtration module and comprising a recirculation tube having a recirculation tube inlet disposed within the storage vessel at a depth selected to extract contents of the storage vessel and having a recirculation tube outlet disposed inside the storage vessel, wherein the recirculation system is configured such that anything in the recirculation system does not pass through the tangential flow filtration module and wherein the recirculation tube inlet and the recirculation tube outlet are located within in the storage vessel such that passage of the contents of the storage vessel through the recirculation system inhibits concentration gradients within the storage vessel, and wherein the recirculation tube outlet terminates in the interior of the storage vessel below a storage vessel fill height.

\* \* \* \* \*